United States Patent [19]

Hodge

[11] Patent Number: 5,413,604
[45] Date of Patent: May 9, 1995

[54] PROSTHETIC KNEE IMPLANT FOR AN ANTERIOR CRUCIATE LIGAMENT DEFICIENT TOTAL KNEE REPLACEMENT

[75] Inventor: W. Andrew Hodge, Palm Beach, Fla.

[73] Assignee: Osteonics Corp., Allendale, N.J.

[21] Appl. No.: 996,980

[22] Filed: Dec. 24, 1992

[51] Int. Cl.$^6$ .............................................. A61F 2/38
[52] U.S. Cl. ..................................................... 623/20
[58] Field of Search ............................. 623/16, 18, 20

[56] References Cited

U.S. PATENT DOCUMENTS

| | | | |
|---|---|---|---|
| 3,748,662 | 7/1973 | Helfet | 623/20 |
| 3,798,679 | 3/1974 | Ewald | 623/20 |
| 3,816,855 | 6/1974 | Saleh | 623/20 |
| 4,219,893 | 9/1980 | Noiles | 623/20 |
| 4,301,553 | 11/1981 | Noiles | 623/20 |
| 4,309,778 | 1/1982 | Buechel et al. | 623/20 |
| 4,883,488 | 11/1989 | Bloebaum et al. | 623/20 |
| 4,950,297 | 8/1990 | Elloy et al. | 623/20 |
| 5,047,057 | 9/1991 | Lawes | 623/20 |
| 5,071,438 | 12/1991 | Jones et al. | 623/20 |
| 5,133,758 | 7/1992 | Hollister | 623/20 |
| 5,133,759 | 7/1992 | Turner | 623/20 |
| 5,133,760 | 7/1992 | Petersen et al. | 623/20 |
| 5,219,362 | 6/1993 | Tuke et al. | 623/20 |

*Primary Examiner*—David Isabella
*Attorney, Agent, or Firm*—Samuelson & Jacob

[57] ABSTRACT

A prosthetic knee implant accommodates and enhances articulation in an anterior cruciate ligament deficient total knee replacement, throughout flexion and extension, by enabling relative axial rotational movement between the femoral component of the implant and the tibial component about an axis generally parallel to the tibia and passing through the lateral compartment of the implant for allowing anterior-posterior displacement of the medial condyle relative to the lateral condyle of the femoral component during articulation of the prosthetic knee implant between flexion and extension in an anterior direction during articulation from extension to flexion and in a posterior direction during articulation from flexion to extension.

20 Claims, 4 Drawing Sheets

PROSTHETIC KNEE IMPLANT FOR AN ANTERIOR CRUCIATE LIGAMENT DEFICIENT TOTAL KNEE REPLACEMENT

The present invention relates generally to prosthetic knee implants and pertains, more specifically, to a prosthetic knee implant having a construction which takes into account the effects of the impairment or absence of the anterior cruciate ligament in a total knee replacement.

The majority of currently available prosthetic knee implants employed for the total replacement of the natural knee joint do not accommodate the anterior cruciate ligament; that is, the anterior cruciate ligament either is sacrificed during the implant procedure or, if preservation is attempted, has been found to rupture within the first several months after implant of the knee prosthesis. Where the anterior cruciate ligament is impaired or completely absent, these currently available nonstabilized total knee replacement prostheses are subject to paradoxical motions in which the femoral condyles translate in a posterior direction in full extension and translate in an anterior direction in flexion, such motions being just the reverse of the motions which occur in the natural knee joint. Thus, as an anterior cruciate ligament deficient knee enters into extension, the medial femoral condyle moves in the posterior direction through a greater translation than the lateral femoral condyle, whereas in the normal condition of the natural knee having a functioning anterior cruciate ligament the lateral femoral condyle translates forward, in an anterior direction, more than the forward movement of the medial femoral condyle. In both instances, the tibia is caused to rotate externally relative to the femur; however, in each instance the translational motions of the condyles differ.

Most currently available total replacement knee implants incorporate a significant incongruence to accommodate any translational motions which may occur during use. The advantage of such a construction is lowered shear stresses at the interfaces between the implant and the natural bone. However, the same construction tends to promote higher articular stresses which can exceed the load-bearing characteristics of the articulating bearing materials, leading to premature failure of the implant. Fully mobile articulating bearings have been employed in an attempt to compensate for higher articulating stresses, but such arrangements introduce a greater potential for dislocation, and the implant procedure generally becomes more complex in that ligament balancing becomes more critical.

The observation that the femoral component and the tibial component of a total knee replacement in which the function of the anterior cruciate ligament is impaired or absent move in a paradoxical fashion has enabled the present invention to provide a prosthetic knee implant which accommodates the particular relative motion experienced between the femoral component and the tibial component in an anterior cruciate ligament deficient knee joint. Whereas the implant of currently available posterior stabilized total knee replacements generally requires the sacrifice of more ligaments and more natural bone in order to accommodate the mechanism which attempts to drive the replacement knee in a more normal fashion, which mechanism usually includes a prominent eminence on the tibial component and a relatively large recess in the femur to accommodate the eminence, thus requiring more radical surgery and increasing the shear stresses encountered at the interface between the implant and the natural bone, the present invention accommodates the motion encountered in an anterior cruciate ligament deficient knee joint, and exhibits several objects and advantages, some of which are summarized as follows: Provides maximum accommodation for movements encountered in a total knee replacement in an anterior cruciate ligament deficient knee joint so as to enhance significantly the functioning of the total knee replacement; enables lower articular wear by increasing articular congruency between the components of the knee prosthesis; improves the range of motion in a total knee replacement; optimizes the function of the posterior cruciate ligament, collateral ligaments, and other remaining ligaments; optimizes the quadriceps mechanism and patella function; optimizes femoral patellar articulation, thus lowering the risk of femoral patellar problems, such as subluxation and increased stress which could lead to excessive patellar wear and fracture; lowers the shear stresses encountered at the interface between the implant components and the natural bone; facilitates the implant procedure and enables implant with more conservative resection of the natural bone; provides a total knee replacement which functions effectively over a longer service life.

The above objects and advantages are attained by the present invention which may be described briefly as a prosthetic knee implant for accommodating and enhancing articulation in an anterior cruciate ligament deficient total knee replacement, throughout flexion and extension, the prosthetic knee implant having a lateral compartment and a medial compartment, the prosthetic knee implant comprising: a femoral component having condyles including a lateral condyle and a medial condyle; a tibial component having articulating surfaces for engagement by the condyles of the femoral component, the articulating surfaces including a lateral articulating surface for engagement by the lateral condyle within the lateral compartment and a medial articulating surface for engagement by the medial condyle within the medial compartment; and rotational means enabling relative axial rotational movement between the femoral component and the tibial component about an axis generally parallel to the tibia and passing through the lateral compartment for allowing anterior-posterior displacement of the medial condyle relative to the lateral condyle in an anterior direction during articulation from extension to flexion and in a posterior direction during articulation from flexion to extension, while engagement is maintained between the corresponding condyles and articulating surfaces, during articulation of the prosthetic knee implant between flexion and extension. In addition, the above arrangement enables the femoral component to be provided with a femoral patellar articulating surface in the patellar compartment of the prosthetic knee implant for engaging the patella to enhance patellar tracking during articulation of the prosthetic knee implant between flexion and extension.

The invention will be understood more fully, while still further objects and advantages will become apparent, in the following detailed description of preferred embodiments of the invention illustrated in the accompanying drawing, in which.

Figure 1:
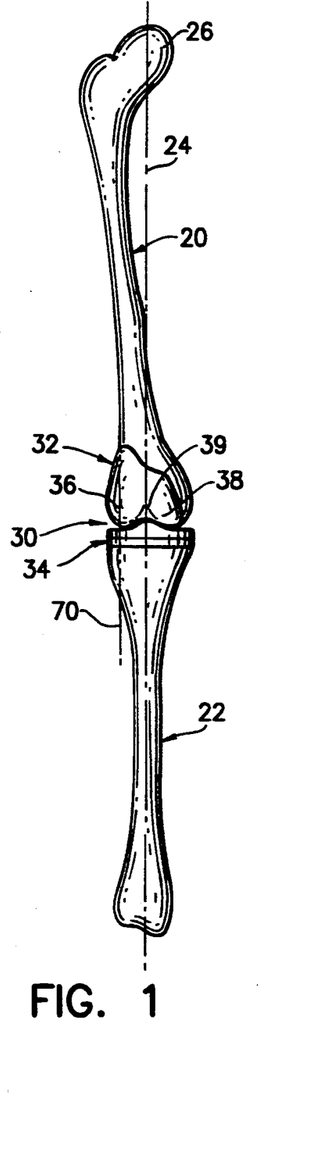
FIG. 1 is a diagrammatic illustration of a prosthetic knee implant constructed in accordance with the present invention and implanted at the joint between a femur and a tibia to provide a total knee replacement.

Referring now the to the drawing, and especially to FIG. 1 thereof, a femur 20 and a tibia 22 extend along a mechanical axis 24 which is generally parallel to the tibia 22 and passes through the head 26 of the natural hip joint. The natural knee joint has been replaced by a knee prosthesis 30 constructed in accordance with the present invention. Knee prosthesis 30 includes a femoral component 32 affixed to the femur 20 and a tibial component 34 affixed to the tibia 22. The femoral component 32 and the tibial component 34 engage one another in a lateral compartment 36 and in a medial compartment 38, in such a manner as to enable the knee prosthesis 30 to serve as a substitute for the natural knee joint for relative movement of the femur 20 and tibia 22 between flexion and extension. In addition, the femoral component 32 includes a femoral patellar compartment 39 within which either the natural patella or a replacement patellar component will engage the femoral component 32, as will be explained in greater detail below.

Figure 2:
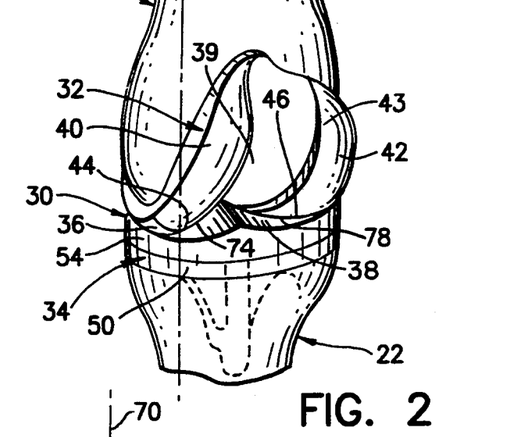
FIG. 2 is an enlarged perspective view of the total knee replacement of FIG. 1.
Figure 3:
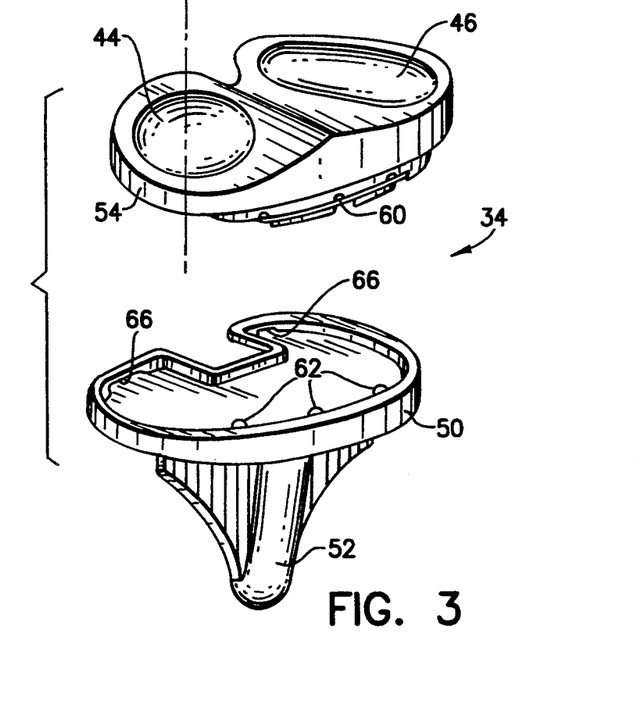
FIG. 3 is an exploded perspective view of the tibial component, including a tibial platform and tibial bearing, of the prosthetic knee implant of FIG. 1.

Turning now to FIGS. 2 and 3, knee prosthesis 30 is a total knee replacement prosthesis, the femoral component 32 providing a replacement lateral condyle 40 and a replacement medial condyle 42, of the femur 20, and a replacement patellar articulating surface 43 between the lateral condyle 40 and the medial condyle 42. The tibial component 34 provides replacement articular surfaces in the form of lateral articular surface 44 for engagement by the lateral condyle 40 within the lateral compartment 36 and medial articular surface 46 for engagement by the medial condyle 42 within the medial compartment 38 of the knee prosthesis 30. To that end, femoral component 32 is affixed to the femur 20 in a now well-known manner. Once the femoral component 32 is so affixed, the natural patella, or a replacement patellar component, as described in greater detail below, will track along the patellar articulating surface 43 within the patellar compartment 39. Where a replacement patellar component is utilized, the natural patella is resurfaced in a now well-known manner.

Tibial component 34 is affixed to the tibia 22 and includes a support member in the form of a platform 50 having a unitary depending stem 52 inserted into the tibia 22 to assist in the accurate location and affixation of the platform 50 on the tibia 22. A bearing member 54 is secured in place on platform 50 to be interposed between the femoral component 32 and platform 50 for providing the lateral and medial articular surfaces 44 and 46 for engagement by the lateral condyle 40 and the medial condyle 42, respectively, to enable articulation of the knee prosthesis 30. The condyles 40 and 42, as well as the replacement patellar articulating surface 43, preferably are constructed of a biocompatible high strength alloy, while the preferred material for bearing member 54, and any replacement patellar component, is a synthetic polymeric material, such as high-density polyethylene, which provides the articular surfaces 44 and 46 with appropriate lubricity characteristics for the proper functioning of knee prosthesis 30. Bearing member 54 may be secured in place on platform 50 by means of any of several well known securing arrangements and is shown secured in place by a lock wire 60 affixed to the bearing member 54 and captured beneath tabs 62 integral with the platform 50 along anterior portions of the platform 50, and by tongues 64 (see FIG. 4) projecting from the bearing member 54 in posterior directions to enter corresponding grooves 66 in posterior portions of the platform 50, all as described in greater detail in U.S. Pat. No. 5,007,933.

In effecting implant of the knee prosthesis 30, the anterior cruciate ligament of the natural knee has been sacrificed. Thus, during articulation of the knee prothesis 30 between flexion and extension the condyles 40 and 42 translate in a posterior direction in full extension and translate in an anterior direction in flexion. As the knee prosthesis 30 enters into extension, the medial condyle 42 moves in the posterior direction through a greater translation than the lateral condyle 40. In order to accommodate such movement, rotational means are provided for enabling relative rotational movement between the femoral component 32 and the tibial component 34 about an axis 70 which is generally parallel to the tibia 22, and to the mechanical axis 24, and which passes through the lateral compartment 36, thereby allowing anterior-posterior displacement of the medial condyle 42 relative to the lateral condyle 40, while engagement is maintained between the corresponding condyles 40, 42 and articulating surfaces 44, 46 during articulation of the knee prosthesis 30 between flexion and extension. Hence, the lateral articulating surface 44 and the lateral condyle 40 have relative configurations for essentially constraining anterior-posterior displacement between the lateral condyle 40 and the lateral articulating surface 44 during articulation of the prosthetic knee prothesis 30, while the medial articulating surface 46 and the medial condyle 42 have relative configurations for accommodating essentially unconstrained anterior-posterior displacement, relative to the essentially constraining relative configurations of the lateral articulating surface 44 and the lateral condyle 40, for anterior-posterior displacement between the medial condyle 42 and the medial articulating surface 46 during articulation of the knee prosthesis 30.

Figure 4:
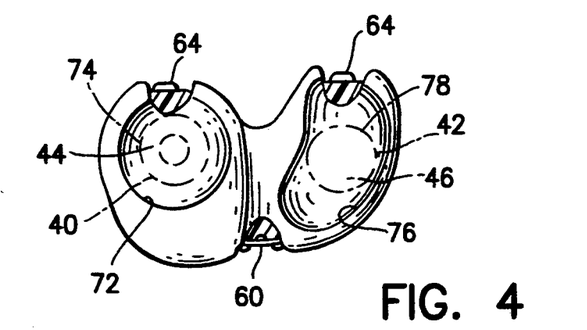
FIG. 4 is a top plan view of the tibial bearing, with portions cut away to show details of construction, and portions of the femoral component shown in phantom.

As best seen in FIG. 4, the lateral articulating surface 44 is provided with a configuration 72 which is generally complementary to and essentially congruent with the counterpart configuration 74 of the lateral condyle 40 so that anterior-posterior displacement between the lateral condyle 40 and the lateral articulating surface 44 during articulation of the knee prosthesis 30 essentially is constrained. In the preferred embodiment, configurations 72 and 74 are generally complementary essentially spherical configurations to assure that the relative configurations of the lateral articulating surface 44 and the lateral condyle 40 essentially constrain relative anterior-posterior displacement between the lateral condyle 40 and the lateral articulating surface 44. The relative configurations of the medial articulating surface 46 and the medial condyle 42 accommodate essentially unconstrained anterior-posterior displacement, as compared to the essentially constraining relative configurations of the lateral articulating surface 44 and the lateral condyle 40. Thus, configuration 76 of the medial articulating surface 46 is elongated in the anterior-posterior direction, relative to the counterpart configuration 78 of the medial condyle 42, and is somewhat arcuate so as to provide a bearing race for the medial condyle 42 as the medial condyle 42 is displaced relative to the medial articulating surface 46 during articulation of the knee prosthesis 30 between flexion and extension.

Figure 5:
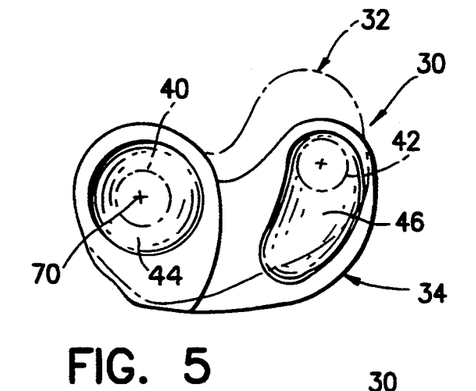
FIG. 5 is a partially diagrammatic, top plan view similar to FIG. 4, but showing the femoral component in phantom so as to illustrate the relationship and function of the component parts.
Figures 6, 7:
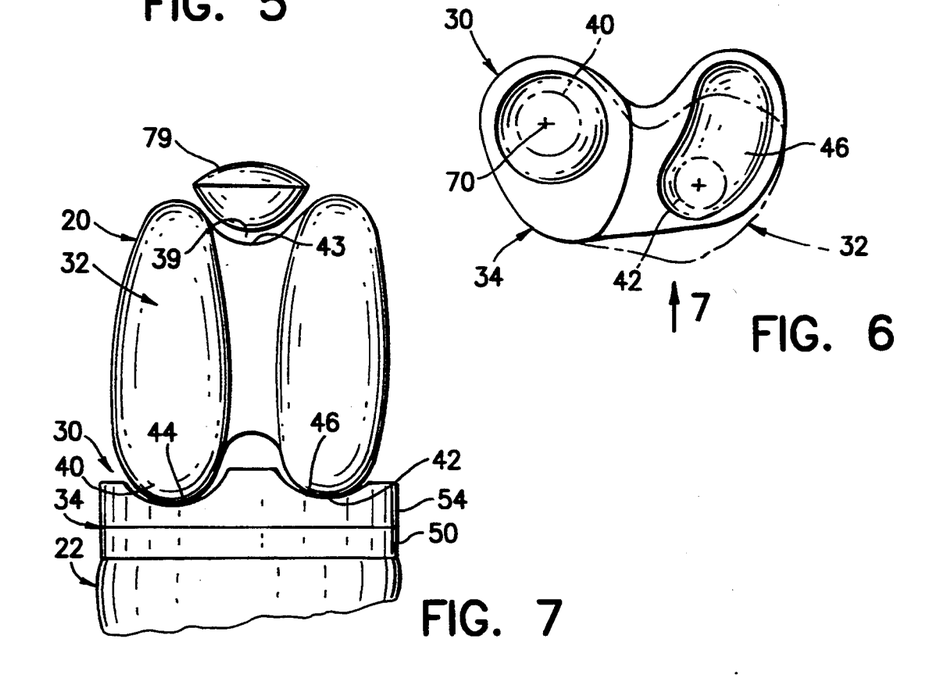
FIG. 6 is a view similar to FIG. 5, but with the component parts in another operating position.
FIG. 7 is a partially diagrammatic elevational view, taken in the direction of the arrow in FIG. 6.
Figure 8:
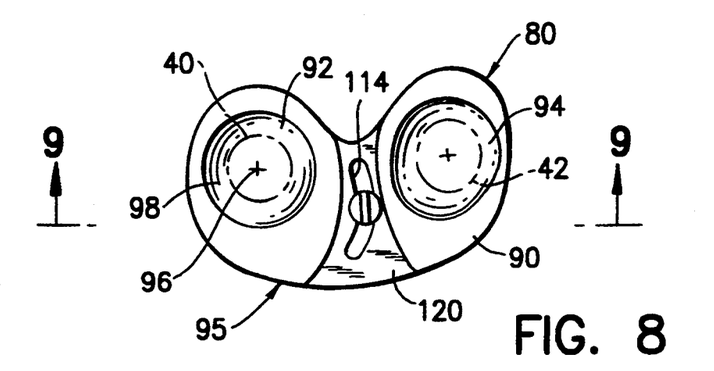
FIG. 8 is a top plan view of a tibial component of another prosthetic knee implant constructed in accordance with the invention and showing another embodiment thereof.
Figure 9:
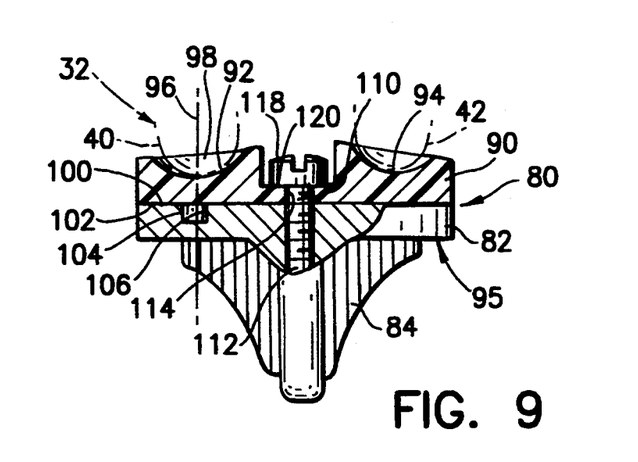
FIG. 9 is an elevational cross-sectional view taken along line 9—9 of FIG. 8, with the addition of portions of the femoral component of the implant, illustrated in phantom.

As illustrated somewhat diagrammatically in FIGS. 5 and 6, at full extension, as seen in FIG. 5, the medial condyle 42 is engaged with the medial articulating surface 46 at a posterior position, while at flexion, as seen in FIG. 6, the medial condyle 42 is engaged with the medial articulating surface 46 at an anterior position. During articulation between flexion and full extension, relative displacement between the lateral condyle 40 and the lateral articulating surface 44 essentially is constrained so that the relative anterior-posterior displacement of the medial condyle 42 along the medial articulating surface 46 between the anterior and posterior positions is by rotation about the axis 70 passing through the lateral compartment 36, and articulating engagement is maintained between the corresponding condyles 40, 42 and articulating surfaces 44, 46 during articulation of the knee prosthesis 30 between flexion and extension.

The relative rotation between the femoral component 32 and the tibial component 34, as described above, enhances patellar tracking; that is, tracking of the natural patella, or a replacement patellar component, illustrated at 79 in FIG. 7, within the patellar compartment 39 is enhanced by the above-described movements of the femoral component 32 and the tibial component 34. In addition, the relatively deep contour of the patellar articulating surface 43 enabled by the configuration of the femoral component 32 further enhances patellar tracking.

In the embodiment illustrated in FIGS. 8 through 11, an alternate tibial component 80 includes a support member in the form of a platform 82 having a unitary depending stem 84 for insertion into the tibia, as discussed above. A bearing member 90 is placed on platform 82 and provides lateral and medial articular surfaces 92 and 94, respectively, for engagement by the lateral condyle 40 and the medial condyle 42, respectively, of femoral component 32 constructed as described above. As in the embodiment of FIGS. 1 through 7, the relative configurations of the lateral articulating surface 92 and the lateral condyle 40 of the femoral component 32 are such that anterior-posterior displacement between the lateral condyle 40 and the lateral articulating surface 92 essentially is constrained during articulation of the knee prosthesis 95. Thus, the lateral articulating surface 92 is constructed with an essentially spherical configuration which is generally complementary and essentially congruent with the configuration of the lateral condyle 40. In the present embodiment, the relative configurations of the medial articulating surface 94 and the medial condyle 42 also are such that anterior-posterior displacement between the medial condyle 42 and the medial articulating surface 94 essentially is constrained during articulation of the knee prosthesis 95. The medial articulating surface 94 also is constructed with an essentially spherical configuration which is generally complementary and essentially congruent with the configuration of the medial condyle 42.

Figure 10:
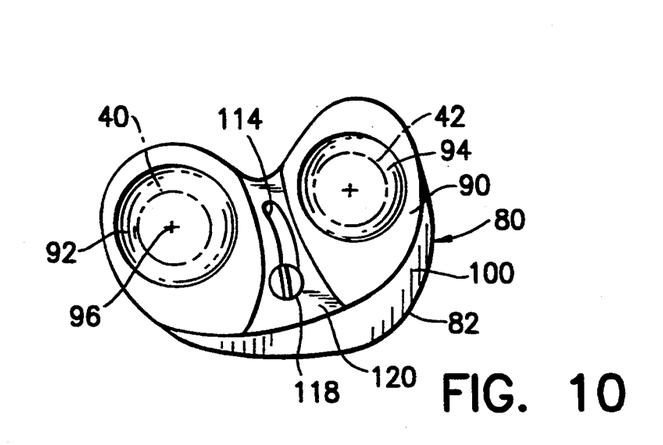
FIG. 10 is a partially diagrammatic, top plan view similar to FIG. 8, but showing portions of the femoral component in phantom so as to illustrate the relationship and function of the component parts.
Figure 11:
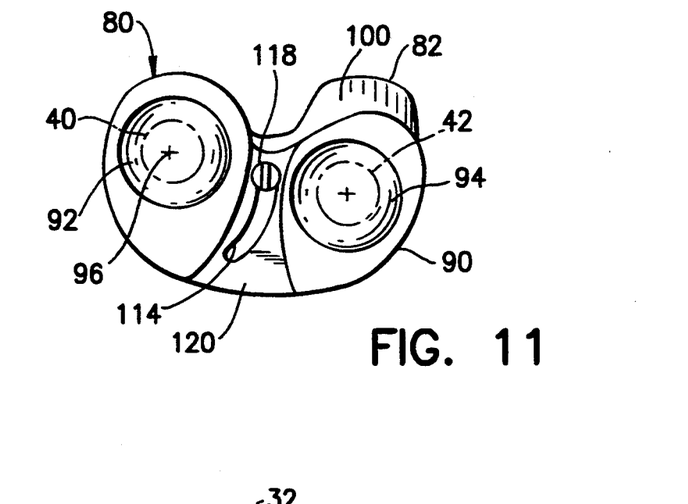
FIG. 11 is a view similar to FIG. 10, but with the component parts in another operating position.

Rotational movement between the femoral component 32 and the tibial component 80 about an axis 96 generally parallel to the tibia and passing through the lateral compartment 98 in order to allow the anterior-posterior displacement of the medial condyle 42 relative to the lateral condyle 40, while maintaining engagement between the corresponding condyles 40, 42 and articulating surfaces 92, 94 during articulation of the knee prosthesis 95 between flexion and extension, as discussed above, is enabled by the following means. Bearing member 90 is seated upon an upper surface 100 of the platform 82 of the tibial component 80, with a lower surface 102 of the bearing member 90 engaged with the upper surface 100 of the platform 82 for relative sliding movement between the bearing member 90 and the platform 82. A pivot pin 104 is integral with the bearing member 90 and depends from the bearing member 90, beneath the lateral compartment 98 of the knee prosthesis 95, for rotational engagement with a complementary socket 106 in the platform 82. The pin 104 and socket 106 are located along axis 96 so that rotational sliding movement of the bearing member 90 relative to the platform 82 is enabled and can take place about axis 96. A post 110 is secured to the platform 82, as by a threaded connection at 112, and passes through an arcuate slot 114 in the bearing member 90, the center of the arc of slot 114 being located at the axis 96. Post 110 includes an integral head 118 which extends radially beyond the edges of the slot 114 and engages the bearing member 90 at the upper surface 120 of the bearing member 90 to capture the bearing member 90 on the platform 82. The arrangement permits pivotal movement of the bearing member 90 relative to the platform 82, about axis 96, within the limits imposed by the arcuate length of slot 114. As illustrated in FIGS. 10 and 11, during articulation of the knee prosthesis 95 between full extension, as seen in FIG. 10, and flexion, as seen in FIG. 11, pivotal movement of the bearing member 90 about the axis 96 accommodates the anterior-posterior displacement of the medial condyle 42 relative to the lateral condyle 40, while engagement is maintained between the corresponding condyles 40, 42 and articulating surfaces 92, 94.

Figure 12:
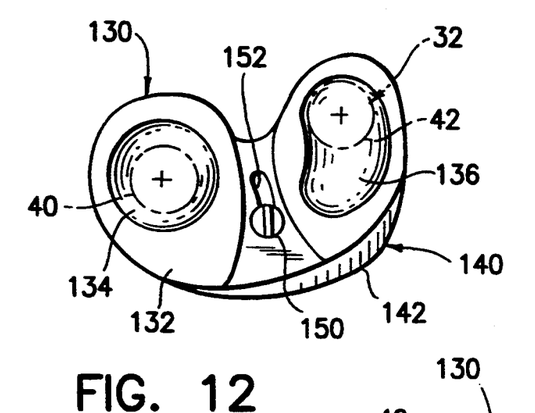
FIG. 12 is a partially diagrammatic, top plan view of still another prosthetic knee implant constructed in accordance with the invention and showing still another embodiment thereof, the tibial component being illustrated in full lines, while portions of the femoral component are shown in phantom.
Figure 13:
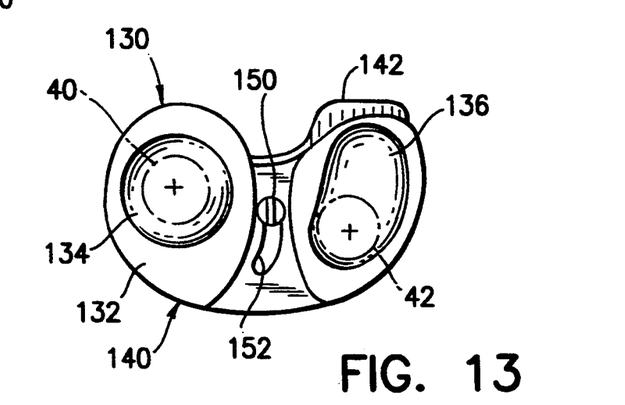
FIG. 13 is a view similar to FIG. 12, but with the component parts in another operating position.

In the embodiment of FIGS. 12 and 13, another alternate tibial component 130 is constructed with features similar to both of the embodiments described above in connection with FIGS. 1 through 11. In the present embodiment, a bearing member 132 provides lateral and medial articular surfaces 134 and 136, respectively, for engagement by the lateral condyle 40 and the medial condyle 42, respectively, of a femoral component 32 constructed as described above. As in the embodiments of FIGS. 1 through 11, the relative configurations of the lateral articulating surface 134 and the lateral condyle 40 of the femoral component 32 are such that anterior-posterior displacement between the lateral condyle 40 and the lateral articulating surface 134 essentially is constrained during articulation of the knee prosthesis 140. The medial articulating surface 136 and the medial condyle 42 have relative configurations which enable limited anterior-posterior displacement between the medial condyle 42 and the medial articulating surface 136 during articulation of the knee prosthesis 140 between full extension, as illustrated in FIG. 12, and flexion, as shown in FIG. 13, thereby accommodating some anterior-posterior displacement of the medial condyle 42 relative to the lateral condyle 40 during articulation of the knee prosthesis 140. At the same time, pivotal means having a construction essentially the same as that described above in connection with the embodiment of FIGS. 8 through 11 enables pivotal movement of the bearing member 132 relative to the platform 142 upon which the bearing member 132 is seated so as to allow further anterior-posterior displacement of the medial condyle 42 relative to the lateral condyle 40 to accommodate the total anterior-posterior displacement of the medial condyle 42 relative to the lateral condyle 40 during articulation of the knee prosthesis 140 between flexion and extension. Thus, the medial articulating surface 136 is elongated in the anterior-posterior direction, relative to the counterpart configuration of the medial condyle 42, and is somewhat arcuate so as to provide a bearing race for the medial condyle 42 as the medial condyle 42 is displaced relative to the medial articulating surface 136 during articulation of the knee prosthesis 140 between flexion and extension. Since pivotal movement of the bearing member 132 relative to the platform 142 of the tibial component 130 enables some anterior-posterior displacement of the medial condyle 42 relative to the lateral condyle 40 during articulation, the medial articulating surface 136 need not be elongated as much as that of the embodiment of FIGS. 1 through 7. Likewise, in a post 150 and slot 152 arrangement, which functions in a manner similar to that described above in connection with the embodiment of FIGS. 8 through 11, the slot 152 need not be arcuately as long as the slot 114 in the bearing member 90 of tibial component 95. However, the length of the medial articulating surface 136 together with the length of the slot 152 accommodate the total anterior-posterior displacement of the medial condyle 42 relative to the lateral condyle 40 during articulation of the knee prosthesis 140 between flexion and extension.

It will be seen that the present invention accomplishes several objects and advantages, some of which have been summarized as follows: Provides maximum accommodation for movements encountered in a total knee replacement in an anterior cruciate ligament deficient knee joint so as to enhance significantly the functioning of the total knee replacement; enables lower articular wear by increasing articular congruency between the components of the knee prosthesis; improves the range of motion in a total knee replacement; optimizes the function of the posterior cruciate ligament, collateral ligaments, and other remaining ligaments; optimizes the quadriceps mechanism and patella function; optimizes femoral patellar articulation, thus lowering the risk of femoral patellar problems, such as subluxation and increased stress which could lead to excessive patellar wear and fracture; lowers the shear stresses encountered at the interface between the implant components and the natural bone; facilitates the implant procedure and enables implant with more conservative resection of the natural bone; provides a total knee replacement which functions effectively over a longer service life.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A prosthetic knee implant for accommodating and enhancing articulation in an anterior cruciate ligament deficient total knee replacement, throughout flexion and extension, the prosthetic knee implant having a lateral compartment and a medial compartment, the prosthetic knee implant comprising:

a femoral component having condyles including a lateral condyle and a medial condyle;

a tibial component having articulating surfaces for engagement by the condyles of the femoral component, the articulating surfaces including a lateral articulating surface for engagement by the lateral condyle within the lateral compartment and a medial articulating surface for engagement by the medial condyle within the medial compartment; and rotational means enabling relative axial rotational movement between the femoral component and the tibial component about an axis generally parallel to the tibia and passing through the lateral compartment for allowing anterior-posterior displacement of the medial condyle relative to the lateral condyle in an anterior direction during articulation from extension to flexion and in a posterior direction during articulation from flexion to extension, while engagement is maintained between the corresponding condyles and articulating surfaces, during articulation of the prosthetic knee implant between flexion and extension.

2. The invention of claim 1 wherein the prosthetic knee implant has a femoral patellar compartment located between the lateral compartment and the medial compartment, and the femoral component includes a patellar articulating surface in the patellar compartment of the prosthetic knee implant for enhancing patellar tracking during articulation of the prosthetic knee implant between flexion and extension.

3. The invention of claim 1 wherein the tibial component includes:

a support member;

a bearing member for interposition between the support member and the femoral component, the articulating surfaces being located on the bearing member for juxtaposition with the condyles of the femoral component; and securing means for securing the bearing member in fixed relationship with the support member;

the lateral articulating surface and the lateral condyle having relative configurations for essentially constraining anterior-posterior displacement between the lateral condyle and the lateral articulating surface during articulation of the prosthetic knee implant; and the medial articulating surface and the medial condyle having relative configurations for accommodating essentially unconstrained anterior-posterior displacement, relative to the essentially constraining relative configurations of the lateral articulating surface and the lateral condyle, for anterior-posterior displacement between the medial condyle and the medial articulating surface during articulation of the prosthetic knee implant.

4. The invention of claim 3 wherein the configurations of the lateral condyle and the lateral articulating surface are generally complementary essentially congruent configurations.

5. The invention of claim 3 wherein the configurations of the lateral condyle and the lateral articulating surface are generally complementary essentially spherical configurations.

6. The invention of claim 3 wherein the prosthetic knee implant has a femoral patellar compartment located between the lateral compartment and the medial compartment, and the femoral component includes a patellar articulating surface in the patellar compartment of the prosthetic knee implant for enhancing patellar tracking during articulation of the prosthetic knee implant between flexion and extension.

7. The invention of claim 1 wherein the tibial component includes:

a support member;

a bearing member for interposition between the support member and the femoral component, the articulating surfaces being located on the bearing member for juxtaposition with the condyles of the femoral component;

the lateral articulating surface and the lateral condyle having relative configurations for essentially constraining anterior-posterior displacement between the lateral condyle and the lateral articulating surface during articulation of the prosthetic knee implant;

the medial articulating surface and the medial condyle having relative configurations for essentially constraining anterior-posterior displacement between the medial condyle and the medial articulating surface during articulation of the prosthetic knee implant; and pivotal means coupling the bearing member with the support member for pivotal movement of the bearing member about the axis passing through the lateral compartment for accommodating the anterior-posterior displacement of the medial condyle relative to the lateral condyle during articulation of the prosthetic knee implant between flexion and extension.

8. The invention of claim 7 wherein the configurations of the lateral condyle and the lateral articulating surface are generally complementary essentially congruent configurations.

9. The invention of claim 8 wherein the configurations of the medial condyle and the medial articulating surface are generally complementary essentially congruent configurations.

10. The invention of claim 7 wherein the configurations of the lateral condyle and the lateral articulating surface are generally complementary essentially spherical configurations.

11. The invention of claim 10 wherein the configurations of the medial condyle and the medial articulating surface are generally complementary essentially spherical configurations.

12. The invention of claim 7 wherein the prosthetic knee implant has a femoral patellar compartment located between the lateral compartment and the medial compartment, and the femoral component includes a patellar articulating surface in the patellar compartment of the prosthetic knee implant for enhancing patellar tracking during articulation of the prosthetic knee implant between flexion and extension.

13. The invention of claim 7 wherein the pivotal means includes a pivot located beneath the lateral compartment.

14. The invention of claim 13 wherein the pivot includes a pin depending from the bearing member and a complementary socket in the support member for receiving the pin in rotational engagement therewith.

15. The invention of claim 1 wherein the tibial component includes:

a support member;

a bearing member for interposition between the support member and the femoral component, the articulating surfaces being located on the bearing member for juxtaposition with the condyles of the femoral component;

the lateral articulating surface and the lateral condyle having relative configurations for essentially constraining anterior-posterior displacement between the lateral condyle and the lateral articulating surface during articulation of the prosthetic knee implant;

the medial articulating surface and the medial condyle having relative configurations for enabling limited anterior-posterior displacement between the medial condyle and the medial articulating surface during articulation of the prosthetic knee implant; and pivotal means coupling the bearing member with the support member for pivotal movement of the bearing member about the axis passing through the lateral compartment for enabling further anterior-posterior displacement of the medial condyle relative to the lateral condyle such that the limited anterior-posterior displacement enabled by the relative configurations of the medial articulating surface and the medial condyle and the further anterior-posterior displacement of the medial condyle relative to the lateral condyle enabled by the pivotal means together accommodate the total anterior-posterior displacement of the medial condyle relative to the lateral condyle during articulation of the prosthetic knee implant between flexion and extension.

16. The invention of claim 15 wherein the configurations of the lateral condyle and the lateral articulating surface are generally complementary essentially congruent configurations.

17. The invention of claim 15 wherein the configurations of the lateral condyle and the lateral articulating surface are generally complementary essentially spherical configurations.

18. The invention of claim 15 wherein the prosthetic knee implant has a femoral patellar compartment located between the lateral compartment and the medial compartment, and the femoral component includes a patellar articulating surface in the patellar compartment of the prosthetic knee implant for enhancing patellar tracking during articulation of the prosthetic knee implant between flexion and extension.

19. The invention of claim 15 wherein the pivotal means includes a pivot located beneath the lateral compartment.

20. The invention of claim 19 wherein the pivot includes a pin depending from the bearing member and a complementary socket in the support member for receiving the pin in rotational engagement therewith.

* * * * *